United States Patent
Franklin et al.

(10) Patent No.: US 6,361,766 B1
(45) Date of Patent: Mar. 26, 2002

(54) ANTIPERSPIRANT FORMULATIONS

(75) Inventors: Kevin Ronald Franklin; Graham Andrew Turner, both of Wirral (GB)

(73) Assignee: Unilever Home & Personal Care, USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/920,778

(22) Filed: Aug. 2, 2001

(51) Int. Cl.$^7$ .............................. A61K 7/32; A61K 7/34; A61K 7/38; A61K 7/00
(52) U.S. Cl. ............................. 424/65; 424/66; 424/68; 424/400; 424/401; 424/DIG. 5
(58) Field of Search .............................. 424/65, 66, 68, 424/400, 401, DIG. 5

(56) References Cited

U.S. PATENT DOCUMENTS

| | | | |
|---|---|---|---|
| 3,255,082 A | 6/1966 | Barton et al. | 167/90 |
| 3,986,203 A | 10/1976 | Davis | 358/10 |
| 4,083,956 A | 4/1978 | Shelton | 424/66 |
| 4,229,432 A | 10/1980 | Geria | 424/68 |
| 4,265,878 A | 5/1981 | Keil | 424/68 |
| 4,425,328 A | 1/1984 | Nabial et al. | 424/68 |
| 4,724,139 A | 2/1988 | Palinczar | 424/66 |
| 4,919,934 A | 4/1990 | Deckner et al. | 424/401 |
| 4,985,238 A | 1/1991 | Tanner et al. | 424/66 |
| 5,486,347 A | 1/1996 | Callaghan et al. | 423/623 |
| 5,833,964 A | 11/1998 | Linn et al. | 424/65 |
| 5,972,319 A | 10/1999 | Linn et al. | 424/65 |
| 6,068,518 A | 5/2000 | Bianchi et al. | 439/660 |

FOREIGN PATENT DOCUMENTS

| | | |
|---|---|---|
| EP | 028 853 | 11/1988 |
| EP | 388 110 | 9/1990 |
| EP | 0 396 137 | 11/1990 |
| EP | 396 137 | 11/1990 |
| EP | 804 921 | 11/1997 |
| GB | 2 291 805 | 2/1996 |
| WO | 98/51272 | 11/1998 |

OTHER PUBLICATIONS

GB Search Report in GB application GB 0019232.8.
Cosmetics ant Toiletries, 1990, vol. 105, pp. 75–78.

*Primary Examiner*—Shelley A. Dodson
(74) *Attorney, Agent, or Firm*—Kevin J. Stein

(57) ABSTRACT

Anhydrous antiperspirant formulations in which a particulate antiperspirant active is suspended in a carrier fluid can result in significant visible deposits when applied to skin or when transferred onto clothing.

Anhydrous antiperspirant suspension sticks which exhibit very low visible deposits are obtainable by employing a carrier fluid in which at least 45% and preferably at least 60% of its weight comprises an oxygen-containing emollient oil having a refractive index of at least 1.465, in conjunction with structurant comprises a wax or a non-polymeric fiber-forming gellant, excluding certain gellants or gellant combinations. Preferred emollient oils include alkyl benzoates and alkylphenylsiloxanes. The waxes can even comprise fatty alcohols.

35 Claims, No Drawings

ANTIPERSPIRANT FORMULATIONS

The present application relates to antiperspirant formulations, and in particular to antiperspirant stick formulations.

BACKGROUND AND PRIOR ART

Topically applied antiperspirant compositions are in widespread use throughout much of the world, in order to enable their users to avoid or minimise visible wet patches on their skin, especially in axillary regions. Antiperspirant formulations containing astringent metal salts such as aluminium or zirconium salts commonly act also as deodorants. Antiperspirant formulations have been produced or proposed for use in several physical forms, such as solids, gels, soft solids, creams, lotions and particulate mixtures and these forms can be applied using a range of different dispensers, including aerosol, roll-on, pump spray, sticks, and barrel dispensers, in accordance with the individual preferences of consumers. In some parts of the world, solid formulations in stick form are especially popular, the stick usually being dispensed from a barrel provided with means to expose the stick above the barrel.

Herein, the term stick indicates a bar of solid material which retains its integrity whilst being applied, i.e. a firm stick and which is commonly, though not exclusively, housed within a dispensing container which hitherto is conveniently in the shape of a barrel. When a portion of a firm stick is drawn across the skin surface, a film of the stick composition is transferred onto the skin surface. Although the stick has the appearance of a solid article, the material forming the stick usually comprises a structured liquid phase such that a film of the material is readily transferred onto another surface such as axillary skin upon contact under pressure.

There are typically three classes of firm antiperspirant sticks, namely suspension sticks, emulsion sticks and solution sticks. Suspension sticks contain a particulate antiperspirant active material suspended in a structured carrier. Emulsion sticks normally comprise an emulsion of an oil phase and a hydrophilic phase containing the antiperspirant active in solution, the continuous phase being structured. In some emulsion sticks, the continuous phase is an oil phase. In solution sticks, the antiperspirant is typically dissolved in the liquid carrier phase which is structured. The liquid phase can comprise water and/or a water-miscible organic solvent. The three categories can be applied to sticks of both firm and soft solids compositions.

Conventionally, many suspension sticks have been structured using naturally-occurring or synthetic waxes, of which typical examples include stearyl alcohol, hydrocarbon waxes, waxes of plant or animal origin or their synthetic analogues or derivatives or silicone waxes. Waxes are widely available, and by suitable selection of the waxes themselves and their concentrations in the formulation can effectively obtain either a soft solid or a firm solid. Thus for example, wax-structured sticks are described in an article in Cosmetics and Toiletries, 1990, vol. 105, p75–78. However, many conventional fatty alcohol or other wax structured sticks tend to leave visible white deposits on application to human skin, and likewise, visible deposits can also be transferred onto clothing by physical contact with the skin. Such visible deposits are disliked by a significant, and in some countries growing, proportion of consumers of antiperspirants, be they on the skin or on clothing. Accordingly, the antiperspirant industry, including the instant inventors, is continuing devoting considerable time and resources to finding means to ameliorate or overcome customer perceived whiteness deposits. In countries where both traditional and low whitening antiperspirant stick products are available, sales of the low whitening formulations have grown relative to traditional formulations.

Patents and patent documents relevant to this field of invention include:

| | |
|---|---|
| U.S. Pat. No. 3,255,082; | Barton et al; |
| U.S. Pat. No. 3,986,203; | Spitzer et al; |
| U.S. Pat. No. 4,083,956, | Shelton; |
| EP-A-0,028,853, | Beckmeyer et al; |
| U.S. Pat. No. 4,425,328, | Nabial et al; |
| U.S. Pat. No. 4,265,878, | Keil; |
| U.S. Pat. No. 4,229,432, | Geria; |
| U.S. Pat. No. 4,724,139, | Palinczar |
| U.S. Pat. No. 4,985,238, | Tanner et; |
| U.S. Pat. No. 5,486,347, | Callaghan et al and |
| U.S. Pat. No. 6,068,518, | Bianchi et al. |

Antiperspirant formulations remain on the skin for considerable periods of time after application, for example many hours before the axilla or other part of the body to which the antiperspirant has been applied is washed. In that respect they differ significantly from many other personal care formulations such as washing or cleansing formulations which are applied and almost immediately removed. Accordingly, all non-volatile components present in the antiperspirant formulations remain on the skin, including not only non-volatile anti-perspirant actives, but also non-volatile components of any carrier fluid which is employed. Such non-volatile components not only remain on the skin, but likewise remain available for transfer onto clothing which comes into contact with the skin. Carrier liquid components can assist in the transfer of solids suspended therein.

Since their introduction, volatile silicone fluids have been widely accepted within the antiperspirants industry as carrier fluids for antiperspirant solids, and commonly are either thickened to form a cream or structured to form a solid in order to suspend particulate antiperspirant materials. Volatile silicone oils have proven to be very popular, on account of their combination of beneficial properties, so that in many or most of the common commercial anhydrous suspension stick formulations, such oils constitute the principal proportion of the carrier fluid. One or more other oils, such as non-volatile silicone oils or non-volatile non-silicone emollient oils are often included or proposed for inclusion in patent specifications in minor amounts in firm stick suspended antiperspirant formulations, and indeed together commonly constitute no more than a minor fraction of the carrier fluid.

Although volatile silicone oils enable the antiperspirant formulations to exhibit many desirable properties, there are two consequences of employing them as the principal component of the carrier fluid, namely that such antiperspirant formulations tend to exhibit comparatively high visible whiteness when they are topically applied and also the visible whiteness of such formulations tends to increase further with the passage of time. Without being bound to any theory, it is believed that increased visible whiteness arises from evaporation of the volatile silicones, thereby exposing those formulation components such as particulate antiperspirant actives and/or structurant which contribute to visible whiteness. These observations are of relevance, because users look carefully at where they are applying antiperspirant formulations, and they often remain on the skin for extended periods of time.

However, it is no simple matter to reformulate antiperspirant formulations with alternative oils. Whilst many oils have been accepted within the industry as minor components of a volatile-silicone-based carrier fluid, the very properties which have rendered them suitable to be considered suitable as emollients have been thought to render them unsuitable as the principal carrier oil. These properties include a propensity to oiliness or greasiness in the resultant product, when present in a large proportion.

A number of attempts have been made already to address the problems of selecting carrier fluids for antiperspirant formulations. Several patent specifications offer lists of emollient oils for incorporation in carrier fluids, in some instances for creams, such as in EP-A-388110 and WO-A-98/51272 and in other instances for sticks, such as U.S. Pat. No. 5,833,964. These specifications classify as similar, materials which the investigation resulting in the present invention show to be significantly different. Accordingly, although such specifications assert that they provide formulation exhibiting low visible deposits, this assertion is often judged against those sticks which were commercially available when the applications were sought and in practice, there often remains considerable room for improvement and do not provide adequate teaching to the skilled formulator to enable that person to choose effectively. Other patent specifications have disclosed the use of certain specified types of hydrocarbons, such as poly alpha olefins in U.S. Pat. No. 4,919,934 and EP-A-804921, in respectively sticks or creams. In view of the feel associated with hydrocarbons, it remains a desideratum to provide formulations which have a lower non-volatile hydrocarbon content.

The visibility of a surface deposit depends on the constituents of the applied formulation, including not only the active constituent and any carrier fluid, but also the structurant that is employed when forming the formulation into a stick. EP-A-396137 (Gillette) discloses compositions which are structured using polyethylene-vinyl acetate copolymers or polyethylene homopolymers or blends, and accordingly provides no teaching for formulations employing waxes and/or non-polymeric fibre-forming structurants as the main or entire structurant. Its examples employ alkylmethyoxy cinnamates as the principle solvent. For the reasons of colour, odour and irritancy identified hereinbelow, it is undesirable to employ methoxy cinnamates in compositions intended for use by the general public, so the skilled man would be prejudiced against this text.

OBJECT OF THE INVENTION

It is an object of the present invention to ameliorate or overcome one or more of the disadvantages of suspension antiperspirant formulations disclosed hereinabove.

It is a further object of at least some embodiments of the present invention to provide a suspension formulation employing a carrier having a non-volatile oil as principal carrier.

BRIEF DESCRIPTION OF THE INVENTION

According to the present invention there is provided an anhydrous antiperspirant formulation comprising a particulate antiperspirant suspended in a water-immiscible carrier fluid which is structured by an effective amount of a structurant, characterised in that at least 45% by weight of said carrier fluid comprises an oxygen-containing emollient oil having a refractive index of at least 1.465, and said structurant is a wax or a fibre-forming gellant other than 12-hydroxystearic acid alone or in combination with stearic acid or a polymeric alkylmethylsiloxane obeying formula (I) or (II) or a combination of β-sitosterol and γ-oryzanol.

Herein, Formula (I) represents

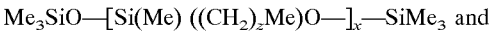

Me$_3$SiO—[Si(Me) ((CH$_2$)$_2$Me)O—]$_x$—SiMe$_3$ and

Formula (II) represents

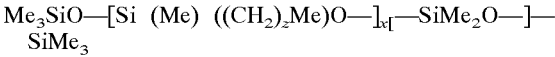

Me$_3$SiO—[Si (Me) ((CH$_2$)$_2$Me)O—]$_y$—SiMe$_2$O—]$_z$—SiMe$_3$ in which x has a value of 1–50, y has a value of 1–100 and z has a value of 10–40.

Herein, the term oxygen-containing emollient oil having a refractive index of at least 1.465 is often abbreviated to HR emollient.

Herein, the refractive index is measured at 22° C., using a refractometer for liquids and a comparative method for solids, unless otherwise specified.

By the choice of such a combination of carrier fluid components and structurant, it has been possible to obtain antiperspirant sticks showing excellently low visible deposits.

In a second aspect of the present invention there is provided a process for the production of an antiperspirant stick comprising the steps of i. incorporating into a liquid carrier a structurant at an effective concentration and in an amount sufficient to structure the carrier to render it solid at 20° C.

ii. rendering the structurant-containing mixture or one or more of its constituents mobile at an elevated temperature iii. mixing the liquid carrier with an antiperspirant active to form an antiperspirant-containing mixture, steps 2 and 3 being conducted either before, after or simultaneously with step 1 iv. introducing the mobile mixture into moulding means and v. cooling or permitting the mobile mixture to cool to a temperature at which it is structured, characterised in that at least 45% by weight of said carrier fluid comprises an oxygen-containing emollient oil having a refractive index of at least 1.465, and said structurant is a wax or a fibre-forming gellant other than 12-hydroxystearic acid alone or in combination with stearic acid or a polymeric alkylmethylsiloxane obeying formula (I) or (II) or a combination of β-sitosterol and γ-oryzanol.

In a third aspect, there is provided a method of reducing or controlling axillary sweating comprising applying topically to skin an anhydrous antiperspirant formulation comprising a particulate antiperspirant suspended in a water-immiscible carrier fluid which is structured by an effective amount of a structurant, characterised in that at least 45% by weight of said carrier fluid comprises of an oxygen-containing emollient oil of higher RI having a refractive index of at least 1.465, and said structurant is a wax or a non-polymeric fibre-forming gellant other than 12-hydroxystearic acid alone or in combination with stearic acid or a polymeric alkylmethylsiloxane obeying formula (I) or (II) or a combination of β-sitosterol and γ-oryzanol.

In a fourth aspect of the present invention there is provided an antiperspirant product comprising an antiperspirant formulation in the form of a stick disposed within a packaging which enables a portion of the stick to be exposed for topical application to skin characterised in that the formulation comprises a particulate antiperspirant suspended in a water-immiscible carrier fluid which is structured by an effective amount of a structurant, characterised in that at least 45% by weight of said carrier fluid comprises of an oxygen-containing emollient oil of higher RI having a refractive index of at least 1.465, and said structurant is a wax or a non-polymeric fibre-forming gellant other than 12-hydroxystearic acid alone or in combination with stearic acid or a polymeric alkylmethylsiloxane obeying formula (I) or (II) or a combination of β-sitosterol and γ-oryzanol.

DETAILED DESCRIPTION OF THE INVENTION AND PREFERRED EMBODIMENTS

The present invention provides antiperspirant sticks structured with wax and/or non-polymeric fibre-forming gellant in which a particulate antiperspirant active is suspended in a carrier fluid comprising a substantial fraction of HR emollient oil or oils.

The choice of the HR emollient oil in a high proportion of the carrier fluid is of importance in the present invention. In essence, the HR emollient oil, or each of the oils if more than one oil is employed, satisfies three criteria. First, it is an anhydrous water-immiscible oil which is fluid at ambient temperature, such as 20° C. Secondly, the oil has a relatively high refractive index, and specifically a refractive index of above 1.465 and thirdly it is oxygen-containing.

By the choice of an HR emollient oil, and by employing it in a high proportion of the carrier fluid, it is possible to obtain sticks with a wide choice of structurant, but which leave no higher than very low visible white deposits on skin or clothing. The ability to have a wide choice of structurant is of considerable benefit to antiperspirant manufacturers in that it means that they are not restricted to a narrow range of materials. The resultant very low visible white deposits, even when employing waxes which have acquired a reputation for leaving high or comparatively high visible white deposits, is manifestly of benefit in view of the prevailing desire expressed by consumers for antiperspirants which do not leave unsightly marks on clothing or on the skin surface.

Many HR emollients have a refractive index of at least 1.47 and most of up to 1.56. A number of especially desirable HR emollient have a refractive index in the region of 1.47 to 1.49. They can be employed individually or mixed together. Yet other desirable HR emollients have a refractive index in the region of 1.50 to 1.56, which can also be used individually or mixed together. If desired, it is possible to employ a mixture of an HR emollient having a refractive index of up to 1.49 with that having a refractive index of at least 1.50. Mixtures of HR emollients can be selected at weight ratios of the individual emollients at the discretion of the formulation maker.

It is highly desirable to employ HR emollients which impart little or no colour to formulations containing them. Accordingly, it is preferred to avoid or minimise the incorporation of alkoxy cinnamates, even if such compounds demonstrate a refractive index of above 1.5, such as by restricting the content of such cinnamates to be alkoxycinnamate deficient by which we mean below 5% of the weight of the carrier fluid, or preferably free from alkoxy cinnamates, by which herein we mean below 1% and especially down to 0%. Such cinnamates tend to be highly coloured, especially in the yellow region of the spectrum, and would render antiperspirant stick less acceptable or even unacceptable to potential consumers. Likewise, there are two further reasons for avoiding or minimising the incorporation of such alkoxy cinnamates. It is desirable to avoid employing or at least minimise the presence of any emollient which has an intrinsically high and unpleasant odour or one which would cause unacceptable irritation.

The proportion of HR emollient in the carrier fluid is at least 45% by weight, and in many desirable formulations is at least 50% or from 55% by weight. If desired, it can comprise as much as 100% of the carrier fluid. However, in practice, the formulation also includes a number of other liquid constituents such as fragrance or other liquid emollients, so that it commonly provides no more than 99% and in a considerable fraction of suitable formulations, up to 95% by weight of the carrier fluid. In a number of formulations, the proportion of HR emollient is at least 60% by weight and more desirably at least 70% by weight and especially at least 80% by weight of the carrier fluid. In a preferred range, the HR emollient comprises from 70 to 99% by weight of the carrier fluid.

The HR emollients of the present invention are oxygen containing, that is to say within the oil there is at least one oxygen atom, which may be embedded within the backbone of the emollient or in a side chain or comprise a substituent. There are two particularly desirable classes of HR emollients, namely a) alkylated or alkoxylated benzoates and b) non-volatile silicone oils. In class a) the oxygen is embedded within a carbon backbone i.e. a C—O—C substructure and within class b) within a silicon backbone, i.e. an Si—O—Si sub-structure.

Within class a) HR emollients, sub groups include alkyl benzoate, alkylene albenzoate, alkoxylated alkyl benzoate or a polyalkylene oxide dibenzoate, or a mixture of two or more sub-classes thereof. The alkyl group often contains at least 10 carbons, in many instances up to 25 carbons. It is often linear, but can alternatively be branched.

Especially desirable alkyl groups are found in the range of from 12 to 20 carbons and include dodecyl (lauryl) terdecyl, tetradecyl (myristyl), pentadecy, hexadecyl (palmityl), octdecyl (stearyl) 2-methyl-heptadecyl (iso-stearyl) and octyldodecyl groups. A mixture of two or more of the alkyl groups can be employed, such as a mixture of C12–15 alkyl groups. The term alkylated herein includes alkylene groups and the latter are terminated at each end with a benzoate group. The alkylene group often contains from 2 to 6 carbons and can be linear or branched, a suitable example of linear being propylene.

In the alkoxylated alkyl benzoates contemplated herein, the alkyl group is terminated by an alkoxy group, which can be monomeric containing for example up to 6 carbons or polymeric such as polyethylene oxide or preferably polypropylene oxide, which conveniently comprises up to 30 units and often from 5 to 20 units. In such compounds, the alkyl group can be selected from the previously identified alkyl groups. Alternatively, the benzoate compound can comprise a polyethylene oxide or polypropylene oxide moiety, or preferably a block copolymer of ethylene oxide and propylene oxide, terminated at each end by a benzoate group. Mixtures of two or more of the benzoate sub-classes of compounds can be employed. This first class of HR emollients tends to have a refractive index in the region of 1.465 to 1.49.

Several preferred benzoate compounds which are HR emollients are available from Finetex under their trade name Finsolv. Although Finsolv P is a yellow liquid, its use appears not to result in formulations having a significant hue.

The second class (b) of HR emollients comprises non-volatile silicone oils. Such compounds commonly comprise alkylphenyl substituted polysiloxanes, and especially methylphenyl polysiloxanes. Desirably, the polysiloxane is short chain and linear, such as a disiloxane, trisiloxane or tetrasiloxane. Particularly desirably, the mole ratio of alkyl (especially methyl) to phenyl substitution is 1:1. It is especially desirable to select within the class of non-volatile polysiloxane materials those which have a viscosity of below 300 centistokes ($300 \times 10^{-6}$ $M^2 s^{-1}$) and advantageously those of below 200 centistokes ($200 \times 10^{-6}$ $M^2 s^{-1}$). In practice, the viscosity of preferred siloxane materials is often in the region of 50 centistokes or higher. The refractive index of preferred non-volatile silicone oils, such as those comprising alkylphenylsiloxanes normally fall within the range of 1.50 to 1.56. Examples of highly preferred non-volatile siloxanes include PDM-7040 and PDM-7050 (trade names) obtainable from Gelest and DC 704 (trade name) obtainable from Dow Corning Inc.

The remaining constituents of the carrier fluid normally comprise other fluids which are miscible with the HR emollient or soluble in the final mixture, thereby forming an anhydrous fluid carrier. Anhydrous herein indicates that the formulation is free from a distinct aqueous phase, which means in practice that it does not comprise an aqueous emulsion or micro-emulsion. The choice of other carrier fluids is at the discretion of the formulator, within the bounds indicated herein. In practice, they tend to be hydrophobic, although a limited proportion of hydrophilic constituents can be employed, such as those materials which, in the chosen proportions, are still miscible with the remainder of the carrier fluid.

Hydrophobic oils which can be employed herein as non-HR component of the carrier fluid have a refractive index of below 1.465, and for ease of reference are sometimes referred to herein as LR oils. In view of the relative proportions of the HR emollients and LR oils in the carrier fluid, the average RI of the carrier is often in the range of from about 1.43 to 1.46. This means that it is not matched to the refractive index of the suspended particulate antiperspirant, so that the observed low scores for visible deposits is normally not achieved by RI matching. It is of considerable value to be able to achieve such good results without RI matching, because it is a particularly difficult problem to match constituents sufficiently closely and consistently in commercial scale production and under commercial operating conditions.

The maximum proportion of LR oils in the carrier fluid is the balance above the proportion provided by the HR emollients. The full breadth of the ranges of proportions for LR oils indicated hereinbelow are attainable only to the extent that the balance above the HR emollient proportion permits this.

One suitable class of LR oil comprises volatile liquid silicones, i.e. liquid polyorganosiloxanes. To class as "volatile" such material should have a measurable vapour pressure at 20 or 25° C. Typically the vapour pressure of a volatile silicone lies in a range from 1 or 10 Pa to 2 kPa at 25° C.

It can be desirable for the carrier fluid to include a volatile silicone because it gives a "drier" feel to the applied film after the composition is applied to skin. The carrier fluid often contains from 0 to 50% and particularly from 10 to 40% by weight volatile silicone Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-7}$ $M^2$/sec (10 centistokes), and particularly above $10^{-7}$ $M^2$/sec (0.1 centistokes), the linear siloxanes normally exhibiting a viscosity of below $5 \times 10^{-6}$ $m^2$/sec (5 centistokes). The volatile silicones can also comprise branched linear or cyclic siloxanes such as the aforementioned linear or cyclic siloxanes substituted by one or more pendant —O—Si($CH_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

Other hydrophobic oils, which can be contemplated to provide at least a part of the non-HR oxygen-containing fraction of the fluid carrier, comprise liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms. Although polyisobutene and polydecene are polymeric in nature, they are mobile liquids at room temperature of 20° C. and do not cause thickening of other hydrophobic oils. Some mineral oils may have an RI which approaches 1.465. Such oils may be used.

Other LR oils can comprise liquid aliphatic esters. Suitable aliphatic esters usually contain at least one long chain alkyl group, such as esters derived from $C_8$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate. The proportion of aliphatic esters in the carrier fluid is often chosen within the range of 0 to 50% and particularly 0 to 25% of the carrier.

Aliphatic alcohols which are liquid at 20° C. may be employed as an LR oil. These include branched chain alcohols of at least 10 carbon atoms e.g. 10 to 25 carbons, such as isostearyl alcohol and octyl dodecanol. The proportion of liquid aliphatic alcohol in the carrier fluid is often chosen within the range of 0 to 50% and particularly 0 to 25% of the carrier.

Other suitable LR oils include aliphatic ethers that are liquid at 20° C., which are derivable from at least one alkanol containing at least 4 carbons and often up to 18 carbons, and which often contain a polyalkylene glycol moiety. Examples of such ethers include myristyl ether derivatives e.g. PPG-3 myristyl ether or lower alkyl ethers of polypropylene glycols such as PPG-14 butyl ether which is commercially available from Amercol under the trade name Fluid AP. The proportion of liquid aliphatic ethers in the carrier fluid is often chosen within the range of 0 to 50% and particularly 0 to 25% of the carrier.

Each of the above-identified classes of LR oils can provide the balance of the carrier fluid. However, it is preferred that at least a fraction of said balance comprises the volatile silicone oil so that the balance generally comprises a mixture of a volatile silicone oil and one of the other LR oils. The weight ratio of volatile silicone oil to other LR oils is often chosen in the range of from 1:4 to 3:1.

Structurants

Waxes

The term "wax" is conventionally applied to a variety of materials and mixtures which have similar physical properties, namely that:

they are solid at 30° C. and preferably also at 40° C.;
they melt to a mobile liquid at a temperature above 30° C. but generally below 95° C. and preferably in a temperature range of 40° C. to 90° C.;
they are water-insoluble and remain water-immiscible when heated above their melting point.

Waxes are usually hydrocarbons, or silicone polymers, or linear fatty alcohols, esters of fatty acids or glyceride derivatives or mixtures containing such compounds, possibly also containing a minority (less than 50%) of other compounds. Naturally occurring waxes are often mixtures of compounds which include a substantial proportion, likely to be a majority, of fatty esters.

A wax forms crystals in the carrier fluid when it cools from the heated state during processing.

These crystals take various forms including needles and platelets depending on the individual waxes. Some waxes form a network of fibrous crystals and can therefore also be identified as fibre-forming structurants.

Examples of hydrocarbon waxes include paraffin wax, microcrystalline wax and polyethylenes with molecular weight of 2,000 to 25,000.

Waxy linear fatty (aliphatic) alcohols normally contain at least 10 and preferably at least 12 carbon atoms, in practice often not more than 40 carbon atoms and many preferred alcohols contain from 14 to 25 carbon atoms. Many formulations which have previously been targeted at low visible white deposits have sought to eliminate altogether or at least severely restrict the proportion of fatty alcohol as wax structurant therein, indicating a preference for below 1% and more preferably zero per cent. It is to the great advantage of the instant invention, that the benefit of very low visible deposits can be achieved whilst still permitting the fatty alcohols to be used as a significant contributor to the structuring (solidification) of the carrier fluid.

Two suitable classes of ester waxes include a) glycerol or glycol esters and b) alkyl alkanoate esters. Within class a) the waxes are selected from fatty acid derivatives of glycerol or glycol, such as ethylene glycol. Preferably at least two ester groups are present in the ester waxes. The fatty acid moiety therein normally contains at least 10 carbons and especially from 12 to 24 carbons. Commonly the esters are derived from stearic acid or benhenic acid or a mixture of fatty acids, such as those containing either or both of said acids e.g. $C_{16}$–$C_{22}$ fatty acids. It is especially desired to employ glycerol esters. Some esters may be present as components in certain naturally occurring waxes and they these may also be made synthetically. A number of suitable waxes are available from Croda Chemicals under their trade name "Synchrowax", e.g. Synchrowax ERLC.

A second class of ester wax comprises esters which have a melting point of at least 30° C. and which satisfy the general formula W1 below:

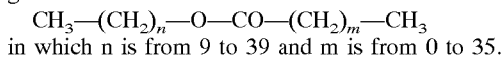

in which n is from 9 to 39 and m is from 0 to 35.

Within general formula W1, a range of preferred esters comprises those in which n is selected within the range of 14 to 24 and especially 16–22 together with m being selected in the range of 14 to 24 and especially 16 to 22. In second range of preferred esters within the general formula, n is selected in the range of 18 to 38 and m is either 0 or 1. It will be understood that mixtures of esters within each preferred range or mixtures of one preferred range of esters with the other can be employed. Some convenient mixtures include a mixture of a wax comprising esters of n=14 to 20 and m=14 to 20 with a wax comprising esters of n=16 to 20 and m=14 to 20 or preferably 16 to 20. A number of alkyl alkanoate ester waxes are available from Koster Keunen under their trade name "Kesterwax", e.g. those having designations K62, K69, K80H, K80P, K82H and K82N. Other suitable waxes within this sub-class are available from Strahl and Pitsch under their trade names SP-C36 and SP-C44 (stearyl stearate and behenyl behenate respectively).

Mixtures of the ester waxes can be employed, either within either class of ester or a mixture of both classes.

A useful class of waxes comprises those which comprise or consist of glyceride waxes and in particular triglyceride waxes. Many suitable glyceride waxes comprise esters of fatty acids, often containing at least 16 carbon atoms, and especially from 18 to 36 carbon atoms. Examples of suitable ester moieties include stearate, eicosinate and behenate. Certain of them can be derived from naturally occurring oils such as castor oil by hydrogenation. Yet others include tristearin, or are obtainable by hydrogenating vegetable oils such as rape seed oil. A number of triglyceride waxes are obtainable from Croda Chemicals under their trade name Syncrowax, e.g. grades HRC and HGL-C.

Examples of natural waxes or simple derivatives of natural products include castor wax, beeswax, carnauba and candelilla waxes, which are of vegetable origin and mineral waxes from fossil remains other than petroleum. Montan wax, which is an example of mineral wax, includes non-glyceride esters of carboxylic acids, hydrocarbons and other constituents. Other naturally available waxes include spermeceti wax, ozokerite, ceresin, baysberry, and synthetic waxes such as Fisher-Tropsch waxes and microcrystalline waxes.

Waxes useful in the present invention will generally be those found to thicken water-immiscible oxygen-containing HR emollient oils such as $C_{12-15}$ alkyl benzoates and/or non-volatile methylphenylpolysiloxanes when dissolved therein (by heating and cooling) at a concentration of 5 to 25% by weight.

The wax is normally employed in such an amount that the carrier fluid is structured in combination with any other structurant that is present and the presence of any particulate antiperspirant and other solids. This amount is usually not greater than the weight of the carrier fluid, and in most instances not greater than 30% of the weight of the composition.

If a wax is used which forms a network of fibres, the amount of it may commonly be from 4 to 12% by weight of the composition. If a wax is used which does not form such a network, for instance a wax which crystallises as spheralitic needles or as small platelets, the amount is often selected in the range of from 4 to 25% and in many preferred embodiments from 5 to 12% or 10 to 25% of the composition, depending at least in part upon whether the wax is being employed in conjunction with or without a further structurant. Silicone waxes are an example of waxes which crystallise as small platelets.

It is often desirable to employ a combination of waxes. Preferred combinations include a combination of a glyceride wax with at least one second wax selected from glycerol ester waxes, alkylalkanoate waxes and fatty alcohols, including specifically those waxes mentioned by name hereinbefore. Preferably, the glyceride wax is present in a weight ratio to the second wax or waxes of 1:2 to 1:6 and more preferably from 2:5 to 1:4.

Fibre-forming Gellants

A number of organic compounds are known to possess the ability to gel water-immiscible organic liquids such as water-immiscible hydrocarbon and/or silicone oils. Such materials are generally non-polymeric, i.e. monomers or dimers with molecular weight below 10,000 often below 5,000 or even 1,000 rather than polymers with more than four repeat units or with molecular weight above 10,000.

Gel formation takes place as an exothermic event within a temperature range referred to as the gel point; upon re-heating, melting of the gel takes place as an endothermic event within a temperature range. Such gels can be disrupted by shearing. Although a small partial recovery may then be observed, such gels do not recover their structure for a long time, if at all, unless re-melted.

Materials with this ability to gel water-immiscible organic liquids have been reviewed by Terech and Weiss in "Low Molecular Mass Gelators of Organic Liquids and the Properties of their Gels" Chem. Rev 97, 3133–3159 [1997] and by Terech in Chapter 8, "Low-molecular weight Organogelators" of the book "Specialist surfactants" edited by I D Robb, Blackie Academic Professional, 1997.

It is characteristic of such non-polymeric gellants (structurants), useful in this invention, that:
- they are able to gel the organic liquid in the absence of any disperse phase, when used in sufficient quantity not exceeding 15% by weight;
- the structured liquids are obtainable by cooling from an elevated temperature at which the structurant is in solution in the liquid - this hot solution being mobile and pourable;
- the (thus obtained) structured liquid becomes more mobile if subjected to shear or stress;
- the structure does not spontaneously recover within 24 hours if the sheared liquid is left to stand at ambient laboratory temperature, even though a small partial recovery may be observed;
- the structure can be recovered by re-heating to a temperature at which the structurant is in solution in the liquid and allowing it to cool back to ambient laboratory temperature.

It appears that such non-polymeric structurants operate by interactions which are permanent unless disrupted by shear or heating. Such structurants form a network of strands or fibres extending throughout the gelled liquid. In some cases these fibres can be observed by electron microscopy, although in other cases the observation of the fibres which are believed to be present is prevented by practical difficulties in preparing a suitable specimen. When observed, the primary fibres in a gel are generally thin (diameter less than 0.5 μm, often less than 0.2 μm) and appear to have numerous branches or interconnections. Primary fibres may entwine to form a thicker strand.

If these fibres are crystalline, they may or may not be the same polymorph as macroscopic crystals obtained by conventional crystallisation from a solvent.

One material which is well known to form such gels is 12-hydroxy stearic acid (12-HSA) which is discussed in Terech et al "Organogels and Aerogels of Racemic and Chiral 12-hydroxy octadecanoic Acid", Langmuir Vol. 10, 3406–3418, 1994. The material is commercially available from Ajinomoto and also from Caschem.

U.S. Pat. No. 5,750,096 is one of several documents which teaches that gelation can be brought about using esters or amides of 12-hydroxy stearic acid. The alcohol used to form such an ester or the amine used to form such an amide may contain an aliphatic, cycloaliphatic or aromatic group with up to 22 carbons therein. If the group is aliphatic it preferably contains at least three carbon atoms. A cycloaliphatic group preferably contains at least five carbon atoms and may be a fixed ring system such as adamantyl.

Other fatty acids with $C_8$ or longer alkyl chains may be used and amides thereof can also be used. A specific example is lauric monoethanolamide also termed MEA lauramide.

N-acyl amino acid amides and esters are employable herein to structure liquids. We have established that they do so by forming fibrous networks. They are described in U.S. Pat. No. 3,969,087. Examples of N-acyl amino acid esters include Nα, Nδ, dicaprylylornithine octyl, decyl, lauryl and stearyl ester, Nα, Nε, -dilauroyllysine hexyl, octyl, decyl, and lauryl esters, Nα, Nε, -di(tallowyl) and Nα, Nε, -di(hydrogenated tallowyl) lysine hexyl, octyl, decyl, and lauryl esters, in which tallowyl indicates the acyl radical of tallow fatty acid.

Examples of N-acylamino acid amides include N-acetyl glutamic acid-α,γ-dilauryl and α,γ-distearyl amides; N-lauroyl glutamic acid diamide, -α,γ-dibutyl, -α,γ-dihexyl, -α,γ-dioctyl, -α,γ-dilauryl and -α,γ-distearyl amides; N-cocoyl glutamic acid, -α,γ-diamide, -α,γ-dibutyl, -α, γ-dihexyl, -α,γ-dioctyl, -α,γ-dilauryl and -α,γ-distearyl amides; N-hydrogenated tallowyl glutamic acid, -α, γ-diamide, -α,γ-dibutyl, -α,γ-dihexyl, -α,γ-dioctyl, -α,γ-dilauryl and -α,γ-distearyl amides; Nα,Nε, -dicaproyllysine amide, butyl hexyl, octyl, lauryl, and stearyl amides; Nα, Nε, -dicaproyloyllysine amide, butyl, dibutyl, hexyl, octyl, lauryl, and stearyl amides; Nα,Nε, -dilauroyllysine amide, butyl, hexyl, octyl, lauryl, and stearyl amides; Nα,Nε, -dicocoyllysine amide, butyl hexyl, octyl, lauryl, and stearyl amides; Nα,Nε, -di(hydrogenated tallowyl) lysine amide, butyl hexyl, octyl, lauryl, and stearyl amides; N-lauroylvaline amide, butyl, hexyl, octyl and lauryl amides; N-lauroyl-phenylalanine amide, butyl, hexyl, octyl and lauryl amides; N-capryloyl leucine amide, butyl, hexyl, octyl and lauryl amides; and N-palmitoylmethionine amide, butyl, hexyl and octyl amides.

N-Lauroyl-L-glutamic acid di-n-butylamide is particularly favoured and is commercially available from Ajinomoto under their trade designation GP-1.

Further materials which have been disclosed as gelling agents are the amide derivatives of di and tribasic carboxylic acids set forth in WO 98/27954 notably alkyl N,N' dialkyl succinamides.

Lanosterol, as disclosed in U.S. Pat. No. 5,635,165 mentioned above may suitably be used if the water-immiscible fluid comprises a major fraction of silicone oils. Lanosterol has the following chemical formula:

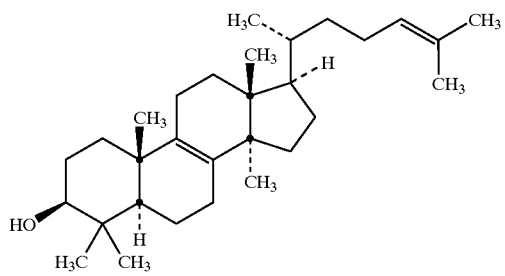

It is commercially available, e.g. from Croda Chemicals Ltd, and as supplied it contains some dihydrolanosterol. This impurity in the commercial material does not need to be removed.

A structurant which is the subject of a co-pending application is a combination of a sterol and a sterol ester. In its preferred form the sterol satisfies either of the two formula.

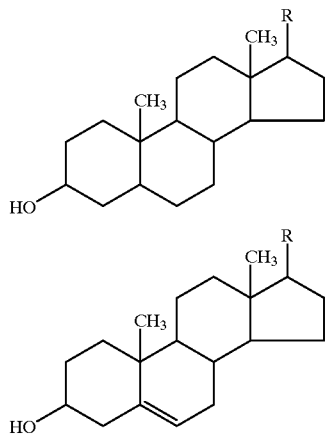

in which R represents an aliphatic, cycloaliphatic or aromatic group, and preferably a linear or branched aliphatic saturated or unsaturated hydrocarbon group. R desirably contains from 1 to 20 carbons and preferably from 4 to 14 carbons.

It is particularly suitable to employ β-sitosterol or campesterol or cholesterol, or a hydrogenated derivative thereof, such as dihydrocholesterol, or a mixture of two or more of them. An especially preferred sterol is β-sitosterol.

The preferred sterol ester is oryzanol, sometimes referred to as γ-oryzanol which contains material satisfying the following formula:

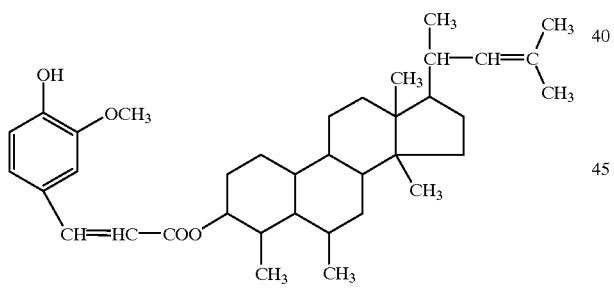

The sterol and sterol ester are used in a mole ratio that is -normally selected in the range of from 10:1 to 1:10, especially from 6:1 to 1:4 and preferably in the range of from 3:1 to 1:2. Employment of the two system constituents within such a mole ratio range, and especially within the preferred range facilitates the co-stacking of the constituents and consequently facilitates the formation of a network that is readily able to structure the formulation.

Another structurant which is the subject of a co-pending application and which may be used in this invention is an ester of cellobiose and a fatty acid, preferably of 6 to 13 carbon atoms especially 8 to 10 carbon atoms. Preferably the cellobiose is fully esterified, or nearly so, and is in the α-anomeric form.

The structure of such a compound, in its α-anomeric form is:

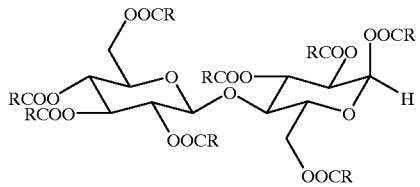

where R is an alkyl or alkenyl chain of 5 to 12 carbon atoms so that the acyl group contains 6 to 13 carbon atoms. Particularly preferred acyl groups incorporate a linear alkyl chain of 7 to 9 carbon atoms and are thus octanoyl, nonanoyl or decanoyl.

The acyl groups may have a mixture of chain lengths but it is preferred that they are similar in size and structure. Thus it is preferred that all of the acyl groups are aliphatic and at least 90% of the acyl groups have a chain length within a range such that the shorter and longer chain lengths in the range differ by no more than two carbon atoms, i.e. length in a range from m−1 to m+1 carbon atoms where m has a value in a range from 7 to 10.

Linear aliphatic acyl groups may be obtained from natural sources, in which case the number of carbon atoms in the acyl group is likely to be an even number or may be derived synthetically from petroleum as the raw material in which case both odd and even numbered chain lengths are available.

Synthetic methods for the esterification of saccharides are well known. The esterification of cellobiose has been reported by Takada et al in *Liquid Crystals*, (1995) Volume 19, pages 441–448. This article gives a procedure for the production of the alpha anomers of cellobiose octa-alkanoates by esterification of β-cellobiose using an alkanoic acid together with trifluoracetic anhydride.

A further example of structurant which is the subject of a co-pending application is compounds of the following general formula (TI):

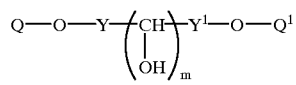

It is preferred that m is 2 so that the structurant compounds comply with a general formula (T2):

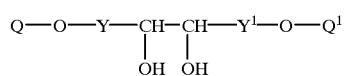

The groups Y and $Y^1$ will usually be identical, i.e. both methylene or both carbonyl. The groups Q and $Q^1$ may not be the same but often will be identical to each other.

If m is 2 and Y and $Y^1$ are methylene groups, the compound is a derivative of threitol, which is 1,2,3,4-tetrahydroxybutane, while if m is 2 and Y and $Y^1$ are carbonyl groups, the compound is a diester of tartaric acid, which is 2,3-dihydroxybutane-1,4-dioic acid.

It is preferred that each group Q and $Q^1$ contains an aromatic nucleus which may be phenyl or, less preferably, some other aromatic group. Thus Q and $Q^1$ may be groups of the formula $$Ar-(CH_2)_n-$$

where Ar denotes an aromatic nucleus, notably phenyl or substituted phenyl and n is from 0 to 10.

An aromatic nucleus (Ar) is preferably unsubstituted or substituted with one or more substituents selected from alkyl, alkyloxy, hydroxy, halogen or nitro.

One substituent may be an alkyl or alkyloxy group with a long alkyl chain. Thus a formula (T3) for preferred structurants of this invention can be given as:

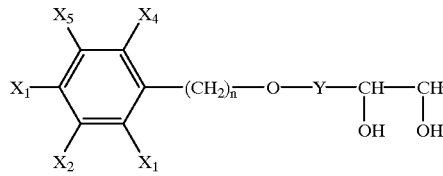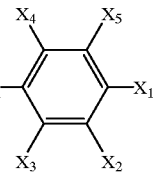

in which
n=0 to 10, preferably 0 to 3, more preferably 1, 2 or 3;
Y=—$CH_2$—O or >C=O
$X_1$ =H, Cl, Br, F, OH, $NO_2$, O—R, or R, where R is an aliphatic hydrocarbon chain with 1 to 18 carbon atoms.
$X_2$ to $X_5$ are each independently H, Cl, Br, F, OH, $NO_2$, $OCH_3$, or $CH_3$ In these formulae above, the central carbon atoms which bear hydroxy groups are chiral centres. Thus if m=2, Y and $Y^1$ are the same and Q and $Q^1$ are the same, the compounds will exist as R,R and S,S optically active forms as well as an optically inactive R,S form.

These compounds may be used as their optically active R,R or S,S forms or as a mixture of the two - which may be a racemic mixture.

Compounds within the general formula (TI) above are available commercially. Also, syntheses of these compounds have been given in scientific literature where the compounds were being used as intermediates for purposes not related to the present invention. Thus syntheses of threitol derivatives can be found in:

Kataky et al, J. Chem Soc Perkin Trans vol. 2 page 321 [1990] Tamoto et al, Tetrahedron Vol. 40 page 4617 [1984], and Curtis et al, J. C. S. Perkin I Vol. 15 page 1756 [1977].

Preparations of tartrate esters are found at:

Hu et al J. Am. Chem. Soc. Vol. 118, 4550 [1996] and Bishop et al J. Org Chem Vol56 5079 [1991].

One structurant which it is eminently desirable to employ in conjunction with a further structurant, be it wax or non-polymeric fibre forming structurant is 12-hydroxystearic acid (abbreviated herein to 12-HSA). It is especially desirable to employ a combination of 12-HSA with either an N-acyl amino acid amide, or with an alkyl alkanoate ester wax. The weight ratio of 12-HSA to the N-acyl amino acid amide is often selected in the weight ratio range of from 1:1 to 5:1. In such combinations, the weight of the 12-HSA is often chosen within the range of 3 to 8% by weight and that of the N-acyl amino acid amide in the range of from 1 to 5% by weight. The weight ratio of 12-HSA to the selected wax is often in the range of 1:1 to 1:3. The weight of 12-HSA in such a combination is often selected in the range of from 3 to 8% by weight and that of the wax from 4 to 12% by weight.

Antiperspirant Actives

An essential constituent of an antiperspirant formulation is an antiperspirant active. Antiperspirant actives are preferably incorporated in an amount of from 0.5–60%, particularly from 5 to 30% or 40% and especially from 5 or 10% to 30 or 35% of the weight of the composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y \cdot wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z \cdot wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_3CH(NH_2)CO_2H$.

It is highly desirable to employ complexes of a combination of aluminium halohydrates and zirconium chlorohydrates together with amino acids such as glycine, which are disclosed in U.S. Pat. No. 3,792,068(Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The proportion of solid antiperspirant salt in a composition normally includes the weight of any water of hydration and any complexing agent that may also be present in the solid active.

In the present invention, the composition takes the form of a suspension in which antiperspirant active in particulate form is suspended in the water-immiscible liquid carrier. Such a composition does not have any separate aqueous phase present and may conveniently be referred to as "substantially anhydrous" although it should be understood that some water may be present bound to the antiperspirant active or as a small amount of solute within the water-immiscible liquid phase. In such compositions, the particle size of the antiperspirant salts often falls within the range of 0.1 to 200 $\mu$m with a mean particle size often from 3 to 20 $\mu$m. Both larger and smaller mean particle sizes can also be contemplated such as from 20 to 50 $\mu$m or 0.1 to 3 $\mu$m.

Optional Ingredients

In addition to the ingredients listed above, the anhydrous, topically-effective compositions of the present invention also can include other optional ingredients that conventionally can be included in topically applied cosmetic compositions. Optional ingredients in compositions of this invention can include disinfectants, for example at a concentration of up to about 10% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as triclosan (Irgasan DP300™), chlorhexidine and Tricloban™, warrant specific mention. A yet another class comprises biguanide salts such as available under the trade mark Cosmosil™.

At the option of the manufacturer, and save as excluded hereinbefore, inclusion of a polymeric structurant can be contemplated. Polymeric structurants which can be employed can comprise organo polysiloxane elastomers such as reaction products of a vinyl terminated polysiloxane and a cross linking agent or alkyl or alkyl polyoxyalkylene-terminated poly(methyl substituted) or poly(phenyl substituted) siloxanes. Suitable elastomers have been disclosed in for example WO 98/00097 and WO 98/18438. A number of polyamides have also been disclosed as structurants for water-immiscible liquids.

It is desirable to include within the formulation one or more wash-off aids, often in a proportion of up to about 10% by weight, especially up to about 5% by weight and particularly from 0.5 to 3% by weight based on the formulation.

Such wash off aids commonly comprise nonionic surfactants and especially nonionic surfactants which contain a polyalkylene oxide moiety, the residue of a fatty acid or fatty alcohol and optionally the residue of an aliphatic polyhydric alcohol linking group. Although, the surfactants may comprise a single fatty residue, they preferably contain two residues. Preferably, the surfactant is an ester surfactant, and especially a diester surfactant. The polyalkylene oxide is often polyethylene oxide, or polypropylene oxide or mixed polyethylene oxide/propylene oxide, the polymer containing from 3 to 50 and especially from 5 to 20 alkylene oxide units. The fatty acid or alcohol often contains from 12 to 24 carbons, and in many instances is linear, examples including 16, 18 or 22 linear carbons. Especially preferred wash-off aids herein comprise polyethylene oxide diesters of fatty alcohols containing 16 to 22 linear carbons, such as PEG-8 distearate.

One important class of optional constituents comprises fragrances. They can be incorporated into the anhydrous, topically-effective compositions in an amount of from 0% to about 5% and often from 0.2 to 1.5% by weight based on the total weight of the composition. Fragrance-containing compositions of the present invention, when applied to skin, fix a substantive fragrance film on the skin that resists moisture, but that can be removed by washing.

One other class of ingredients comprises moisturising agents such as humectants. These include propylene glycol, sorbitol and especially glycerol. Moisturising agents often comprise from 0 to 5% by weight of the formulation, and if employed, it is desirable that the amount is chosen such that the agent is retained within the carrier fluid.

Yet other optional ingredients that can be included in the anhydrous composition of the present invention include, but are not limited to, drying agents, like talc or DRY FLO (aluminium starch octenylsuccinate); preservatives; and dyes. Generally, such optional ingredients are present in a composition of the present invention in an amount of about 10% or less by weight. In addition, an organoclay can be included in a composition of the present invention as an additional suspending agent in an amount of up to 20% by weight of the composition. An organoclay is potentially helpful as an anti-caking agent to maintain a particulate topically-effective compound homogeneously dispersed throughout the composition. An exemplary organoclay is a quaternised three-layer clay exfoliated with a polar solvent, like a quaternised montmorillonite clay exfoliated with propylene carbonate. Such clays are available under the trade name "Bentone". Other inorganic materials which can be incorporated, for example as a thickener for the formulation, comprise particulate silica, such as fumed silica, suitably in an amount of up to 5%.

Still other cosmetic adjuncts can include:
  skin feel improvers, such as talc (mentioned hereinabove) or finely divided polyethylene, or glyceryl fatty esters, e.g. glyceryl stearate, incorporated, for example, in an amount of up to about 10% w/w;
  skin benefit agents such as allantoin or lipids, for example in an amount of up to 5% w/w; and
  skin cooling agents, such as menthol and menthol derivatives, often in an amount of up to 2% w/w.

Many of the stick formulations produced in accordance with the present invention are opaque. However, it is possible to obtain sticks having an appearance which is at least slightly translucent, for example by so selecting the constituents of the carrier fluid and the nature of the antiperspirant active that the refractive index of the carrier fluid and dispersed solid differs by no more than about 0.06, preferably employing antiperspirant active particulates which lack substantial internal voids. Substantially internal void-free actives can be obtained by milling void-containing actives.

Whilst the ingredients disclosed herein are effective for preparing the antiperspirant formulations of the instant invention, prospective manufacturers should keep abreast of advances in scientific understanding of their effect on humans and particularly on skin before selling the resultant compositions for topical application to skin.

The compositions described herein can be produced by conventional processes for making suspension solid sticks. A convenient process sequence for suspension antiperspirant formulations comprises first mixing the structurant or mixture of structurants, namely the wax(es), the non-polymeric fibre-forming gellant(s) or a mixture of both with the carrier at a temperature that is high enough to melt the structurant. Thereafter, particulate antiperspirant active can be blended with the carrier solution and the blend is formed into a solid mass by cooling, for example by being introduced into its dispensing container at a temperature that is often 5 to 10° C. above its normal setting temperature. The process normally includes a suitable filling process, such as a pour fill process (sometimes gravity -fed injection) or injection at elevated pressure into a dispensing container such as a barrel where it is cooled or allowed to cool to ambient.

The compositions herein are suitable for applying topically to human skin, and particularly antiperspirant compositions to axillae, thereby reducing observable perspiration.

Product Packages

The compositions of this invention are structured liquids which are firm in appearance. A composition of this invention will usually be marketed as a product comprising a container with a quantity of the composition therein, where the container has an aperture for the delivery of composition, and means for urging the composition in the container towards the delivery aperture. Conventional containers take the form of a barrel of oval cross section with the delivery aperture(s) at one end of the barrel. An alternative cross section is round.

A composition of this invention is typically sufficiently rigid that it is not apparently deformable by hand pressure. It is suitable for use as a stick product in which a quantity of the composition in the form of a stick is accommodated within a container barrel having an open end at which an end portion of the stick of composition is exposed for use. The opposite end of the barrel is closed.

Generally the container will include a cap to cover its open end and a component part which is sometimes referred to as an elevator or piston fitting within the barrel and capable of relative axial movement along it. In such packaging, the stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston. One transport mechanism comprises a threaded rod which extends axially into the stick through a correspondingly threaded aperture in the piston, and means mounted on the barrel for rotating the rod. Conveniently, the rod is rotated by means of a hand-wheel mounted on the barrel at its closed end, i.e. the opposite end to the delivery opening.

The component parts of such containers are often made from thermoplastic materials, for example polypropylene or polyethylene.

Having described the invention in general terms, specific embodiments thereof will now be described in some detail by way of example only.

List of Ingredients—Trade Name, INCI Name, Supplier

1) Syncrowax ERLC, $C_{18-36}$ glycol esters (Croda)
2) Castorwax MP80, hydrogenated castor oil (CasChem)
3) Kesterwax K82H, $C_{20-40}$ alkyl stearate (Koster Keunen)
4) Kesterwax K62, $C_{16-22}$ alkyl stearate behenate (Koster Keunen)
5) Stearyl alcohol (Henkel)
6) 12-hydroxystearic acid (CasChem)
7) GP-1, N-lauryl-L-glutamic acid di-n-butyl amide (Ajinomoto)
8) AZAG 7167, Al/Zr tetrachlorohydrex glycine complex (Summit)
9) SuprafinoTalc, talc (Luzenac Inc)
10) Finsolv TN, C12–15 Alkyl Benzoate (Finetex) [RI=1.4841]
11) DC245, cyclomethicone (Dow Corning Inc) [RI=1.3997]
12) Fluid AP, PPG-14 Butyl Ether, (Amercol) [RI=1.4465]
13) Silkflo 364 NF, polydecene (Albemarle) [RI=1.4544]
14) DC704, tetramethyltetraphenyltrisiloxane (Dow Corning Inc) [RI=1.5558]
15) Eutanol G, octyldodecanol (Henkel) [RI=1.4538]
16) Prisorine 3515, isostearyl alcohol (Unichema) [RI=1.4559]
17) $C_{24-34}$ Montan Acid Wax (Clariant)
18) AACH A418 (Summit)
19) Glycerol (Aldrich) [RI=1.4725]
20) Finsolv BOD, octyl dodecyl benzoate (Finetex) [RI=1.4839]
21) Finsolv SB, isostearyl benzoate (Finetex) [RI=1.4860]
22) Finsolv P, PPG-15 stearyl ether benzoate (Finetex) [RI=1.4668]
23) Finsolv TPP, mixture of $C_{12-15}$ Alkyl Benzoate/dipropylene glycol dibenzoate/PPG-15 stearyl ether benzoate (Finetex) [RI=1.4915]
24) Finsolv Expt 117–136, Experimental grade mixture of $C_{12-15}$ Alkyl Benzoate/poloxamer 182 dibenzoate (Finetex) [RI=1.4860] {poloxamer 182 dibenzoate is a dibenzyl ester of an EO/PO block co-polymer}
25) Mineral Oil, Sirius M70 (Dalton) [RI=1.4625]
26) Kesterwax K80H, C20–40 alkyl stearate (Koster Keunen)
27) Reach 908, Al/Zr tetrachlorohydrex glycine complex (Reheis)
28) DC705, trimethypentaphenyltrisiloxane (Dow Corning) [RI=1.5620]
29) DM 7040, tetramethyltetraphenyltrisiloxane (Gelest) [RI=1.5554]
30) PDM 7050, trimethypentaphenyltrisiloxane (Gelest) [1.5625]
31) SP-C44 Ester Wax, Behenyl Behenate, (Strahl and Pitsch)
32) Cutina MD, Glyceryl stearate, (Henkel)
33) Estol EO4DS 3724, PEG8 Distearate, (Unichema)
34) Aerosil 200, Fumed Silica, (Degussa)
35) SF1642, Silicone wax, (General Electric)

General Preparative Method

The preparations in Examples 1 to 4 and Comparisons CA to CB were made by the general preparative route or by the modification indicated below.

The structurant or structurants were weighed into a round-bottomed flask or a beaker. The amounts of carrier oil(s) were then weighed into the flask, and the mixture was stirred with an overhead stirrer and heated using a isomantle or hotplate until all of the structurant had dissolved. The source of heat was then removed and the mixture left to cool to about 85° C. While still stirring the weighed amount of the particulate antiperspirant active, and where appropriate other particulate materials, including talc, was or were then added with stirring into the hot mixture. The mixture was permitted to cool until its temperature had reached about 10° C. above the solidification temperature of the formulation, judged either a trial run or on the basis of experience with other formulations using the same structurant(s), temperature sensitive ingredients such as the perfume were added using a Pasteur pipette. The mixture continued to be stirred and cool and was poured into stick barrels at approximately 5° C. above its normal solidification temperature, i.e. solidification at 1 atmosphere pressure and without being subjected to treatment which can alter the solidification temperature. The sticks were then left to cool in the laboratory and solidify. Characterisation was carried out when the sticks had been stored at room temperature for at least 24 hours.

When using the foregoing general preparative process to make Certain of the formulations containing ingredient 7, GP-1 as a structurant, solidified prematurely when the antiperspirant solids were introduced after the molten mixture had cooled to about 10° C. above its normal solidification temperature, so that for those formulations, the preparation was repeated, but adding the antiperspirant to the molten mixture that was held at a temperature above 85° C.

EXAMPLE 1

Wax Structured Opaque Sticks

The formulations made in Example 1 and their properties are summarised in Table 1 below.

CWS=Commercially available conventional white solid stick, structured with waxes (stearyl alcohol+castor wax) employing a mixture of volatile silicone oils as the principal carrier fluid.

ISS=Commercially available solid stick with lower visible deposits, structured with waxes (stearyl alcohol+castor wax) and employing as carrier fluid a mixture of volatile silicone oils (refractive index of about 1.4) with a non-volatile masking oil (refractive index of below 1.465) (Fluid AP) at a weight ratio of about 4:1. nm=measurement not made Comp CA: Stick cracked and fell apart, so that no characterisation measurements could be made.

TABLE 1

|  | Comp CWS | Comp ISS | Comp CA | Comp CB | Ex 1.1 | Ex 1.2 | Ex 1.3 | Ex 1.4 |
|---|---|---|---|---|---|---|---|---|
| Syncrowax (1) | | | | | | | | |
| Castorwax (2) | | | 4.5 | 4.5 | 5 | 4 | 3 | 4.5 |
| K82H (3) | | | 13.5 | 13.5 | 15 | 12 | 0 | 13.5 |
| AZAG 7167 (8) | | | 24 | 24 | 24 | 24 | 24 | 24 |
| Finsolv TN (10) | | | | 11.4 | 22.8 | 55 | 59 | 63 | 57 |
| DC245 (11) | | | 45.6 | 34.2 | | | | |
| Perfume | | | | 1 | 1 | 1 | 1 | 1 | 1 |
| Penetrometer Hardness (mm) | 9.8 | 6.8 | nm | 11.2 | 6.5 | 8.7 | 11.1 | 8.3 |
| Whiteness on Black Wool | 165.5 | 42.7 | nm | 50.7 | 15.5 | 19.3 | 22.2 | 16.3 |
| Whiteness grey abrasive paper | 131.0 | 60.2 | nm | 40.1 | 32.3 | 29.1 | 36.3 | 28.6 |

|  | Ex 1.5 | Ex 1.6 | Ex 1.7 | Ex 1.8 | Ex 1.9 | Ex 1.10 | Ex 1.11 | Ex 1.12 |
|---|---|---|---|---|---|---|---|---|
| Syncrowax (1) | | | | | | | | 15 |
| Castorwax (2) | 4.5 | 4.5 | 4.5 | 4.5 | 4.5 | 4.5 | 4 | 5 |
| K82H (3) | 13.5 | 13.5 | 13.5 | 13.5 | 13.5 | 13.5 | 12 | |
| AZAG 7167 (8) | 24 | 24 | 24 | 24 | 24 | 24 | 24 | 24 |
| Finsolv TN (10) | 45.6 | 39.9 | 34.2 | 28.5 | 45.6 | 45.6 | 47.2 | 55 |
| DC245 (11) | 11.4 | 17.1 | 20.8 | 28.5 | | | 11.8 | |
| Fluid AP (12) | | | | | 11.4 | | | |

TABLE 1-continued

| Silkflo 364NF (13) | | | | | 11.4 | | | |
|---|---|---|---|---|---|---|---|---|
| Perfume | 1 | 1 | 1 | 1 | 1 | 1 | 1 | 1 |
| Penetrometer Hardness (mm) | 8.8 | 8.5 | 8.9 | 9.3 | 6.0 | 7.4 | 8.2 | 8.0 |
| Whiteness on Black Wool | 16.1 | 20.1 | 18.7 | 20.3 | 20.6 | 23.3 | 20.6 | 14.5 |
| Whiteness grey abrasive paper | 37.2 | 37.3 | 32.9 | 31.4 | 33.4 | 32.5 | 36.7 | 31.2 |

|  | Ex 1.13 | Ex 1.14 | Ex 1.15 | Ex 1.16 | Ex 1.17 | Ex 1.18 | Ex 1.19 | Ex 1.20 |
|---|---|---|---|---|---|---|---|---|
| Syncrowax (1) | 12 | 9 | 13.5 | 13.5 | 13.5 | 13.5 | 13.5 | 13.5 |
| Castorwax (2) | 4 | 3 | 4.5 | 4.5 | 4.5 | 4.5 | 4.5 | 4.5 |
| AZAG 7167 (8) | 24 | 24 | 24 | 24 | 24 | 24 | 24 | 24 |
| Finsolv TN (10) | 59 | 63 | 57 | 45.6 | 39.9 | 45.6 | 45.6 | 55 |
| DC245 (11) | | | | 11.4 | 17.1 | | | |
| Fluid AP (12) | | | | | | 11.4 | | |
| Silkflo 364NF (13) | | | | | | | 11.4 | |
| Talc (9) | | | | | | | | 1 |
| Perfume | 1 | 1 | 1 | 1 | 1 | 1 | 1 | 1 |
| Penetrometer Hardness (mm) | 8.7 | 11.2 | 8.7 | 9.2 | 9.7 | 9.8 | 9.4 | 8.7 |
| Whiteness on Black Wool | 16.8 | 16.2 | 15.8 | 16.6 | 13.3 | 15.1 | 15.7 | 14.0 |
| Whiteness on grey abrasive paper | 31.7 | 29.9 | 28.6 | 32.0 | 32.6 | 30.1 | 30.2 | 39.7 |

|  | Ex 1.21 | Ex 1.22 | Ex 1.23 | Ex 1.24 | Ex 1.25 | Ex 1.26 | Ex 1.27 | Ex 1.28 |
|---|---|---|---|---|---|---|---|---|
| Castorwax (2) | 4.5 | 6 | 6 | 4.5 | 4.5 | 4.5 | 4 | 4.5 |
| K82H (3) | 13.5 | | | 13.5 | 13.5 | 13.5 | | |
| Stearyl Alcohol (5) | | 15 | 15 | | | | | |
| K80H (26) | | | | | | | 12 | 13.5 |
| AZAG 7167 (8) | 24 | 24 | 24 | 24 | 24 | 24 | | |
| AZAG 908 (27) | | | | | | | 24 | 24 |
| Finsolv TN (10) | 55 | 54 | 37.8 | | 28.5 | | 59 | 28.5 |
| DC245 (11) | | | 16.2 | | 28.5 | | | 28.5 |
| DC704 (14) | | | | 57 | 28.5 | 28.5 | | |
| Talc (9) | 1 | | | | | | | |
| Perfume | 1 | 1 | 1 | 1 | 1 | 1 | 1 | 1 |
| Penetrometer Hardness (mm) | 8.4 | 9.2 | 10.0 | 3.6 | 4.8 | 7.7 | 11.8 | 14.6 |
| Whiteness on Black Wool | 18.8 | 18.6 | 17.6 | 15.0 | 14.9 | 16.2 | 21.7 | 21.2 |
| Whiteness on grey abrasive paper | 28.6 | 35.3 | 34.9 | 36.9 | 38.7 | 33.5 | 26.6 | 32.3 |

|  | Ex 1.29 | Ex 1.30 | Ex 1.31 | Ex 1.32 | Ex 1.33 | Ex 1.34 | Ex 1.35 | Ex 1.36 |
|---|---|---|---|---|---|---|---|---|
| Syncrowax (1) | | | 13.5 | 13.5 | 13.5 | 13.5 | 13.5 | |
| Castorwax (2) | 4 | 3 | 4.5 | 4.5 | 4.5 | 4.5 | 4.5 | 4.5 |
| K82H (3) | | | | | | | | 13.5 |
| K80H (26) | 12 | 9 | | | | | | |
| AZAG 7167 (8) | 24 | 24 | 24 | 24 | 24 | 24 | 24 | 24 |
| Finsolv TN (10) | | | | | | | 28.5 | 55 |
| Finsolv BOD (20) | 59 | | | | | | | |
| Finsolv SB (21) | | 57 | | | | | | |
| Finsolv TPP (22) | | | 57 | | | | | |
| Finsolv P (23) | | | | 57 | | | | |
| Finsolv Expt 117-136 (24) | 1 | | | | 57 | | | |

TABLE 1-continued

|  | | | | | | | | |
|---|---|---|---|---|---|---|---|---|
| Mineral Oil (25) | | | | | | 28.5 | | |
| DC245 (11) | 12.0 | | | | | | | |
| DC704 (14) | | 63 | | | | | | |
| Glycerol (19) | 25.2 | | | | | | | 2 |
| Perfume | 27.8 | 1 | 1 | 1 | 1 | 1 | 1 | 1 |
| Penetrometer Hardness (mm) | 12.0 | 9.6 | 14.1 | 15.2 | 9.5 | 13.5 | 13.0 | 9.6 |
| Whiteness on Black Wool | 25.2 | 18.9 | 21.7 | 20.3 | 22.5 | 23.0 | 22.2 | 12.2 |
| Whiteness on grey abrasive paper | 27.8 | 29.1 | 29.6 | 31.9 | 33.5 | 30.5 | 35.5 | 31.6 |

|  | Ex 1.37 | Ex 1.38 | Ex 1.39 | Ex 1.40 | Ex 1.41 | Ex 1.42 | Ex 1.43 |
|---|---|---|---|---|---|---|---|
| Syncrowax (1) | | | 13.5 | | | | |
| Castorwax (2) | 4 | 4 | 4.5 | 3 | 3 | 3 | 3 |
| K82H (3) | 12 | 12 | | | | | |
| K80H (26) | | | | 9 | 9 | 9 | 9 |
| AZAG 7167 (8) | 24 | 24 | 24 | 24 | 24 | 24 | 24 |
| Finsolv TN (10) | 29.5 | | | | 31.5 | | |
| Finsolv BOD (20) | | | 59 | 57 | | | |
| DC245 (11) | 29.5 | | | | | | |
| DC705 (28) | | | | 63 | 31.5 | | |
| PDM 7040 (29) | | | | | | 63 | |
| PDM 7050 (30) | | | | | | | 63 |
| Perfume | 1 | 1 | 1 | 1 | 1 | 1 | 1 |
| Penetrometer Hardness (mm) | 17.7 | 10.7 | 13.9 | 4.9 | 9.7 | 6.9 | 5.6 |
| Whiteness on Black Wool | 15.9 | 23.8 | 20.6 | 15.3 | 13.4 | 13.3 | 17.5 |
| Whiteness on grey abrasive paper | 31.7 | 27.4 | 28.2 | 25.8 | 27.6 | 31.9 | 28.2 |

TABLE 1-continued

|  | Ex 1.44 | Ex 1.45 | Ex 1.46 | Ex 1.47 | Ex 1.48 | Ex 1.49 |
|---|---|---|---|---|---|---|
| Castorwax (2) | 12 | 10 | 8 | 6 | | 4.0 |
| K80H (26) | 4 | 6 | 8 | 10 | 16 | |
| SP-C44 Ester Wax (31) | | | | | | 17.5 |
| AZAG 7167 (8) | 24 | 24 | 24 | 24 | 24 | |
| AZAG 908 (27) | | | | | | 24.0 |
| Finsolv TN (10) | 59 | 59 | 59 | 59 | 59 | 47 |
| DC245 (11) | | | | | | 6.5 |
| Perfume | 1 | 1 | 1 | 1 | 1 | 1 |
| Penetrometer Hardness (mm) | 10.6 | 9.1 | 9.6 | 9.8 | 6.7 | 9.2 |
| Whiteness on Black Wool | 15.4 | 15.0 | 16.6 | 18.0 | 18.0 | 25.0 |
| Whiteness on grey abrasive paper | 25.0 | 28.2 | 25.0 | 27.4 | 30.8 | 35.6 |

Sticks Ex 1.1 to Ex 1.49 all left virtually no white deposits when applied to skin. By comparison, the sticks of commercial Comparisons CA and CB, and formulations outside the scope of the present invention showed significantly inferior visible deposits or were physically not able to be tested.

EXAMPLE 2

Opaque Sticks Structured with a Non-polymeric Fibre-forming Gellant Alone or with a Wax The formulations and resultant properties of sticks made in Example 2 are summarised in Table 2 below.

TABLE 2

|  | Ex 2.1 | Ex 2.2 | Ex 2.3 | Ex 2.4 | Ex 2.5 | Ex 2.6 | Ex 2.7 | Ex 2.8 | Ex 2.9 |
|---|---|---|---|---|---|---|---|---|---|
| 12-HSA (6) | 6 | 6 | 6 | 6 | 6 | 6 | 6 | 6 | |
| GP-1 (7) | | | | | | | | | 6 |
| K62 (4) | 8 | 8 | 8 | 8 | | | | | |
| K82H (3) | | | | | 8 | 8 | 8 | 8 | |
| AZAG 7167 (8) | 24 | 24 | 24 | 24 | 24 | 24 | 24 | 24 | 24 |
| Finsolv TN (10) | 61 | 34.9 | 48.8 | 36.6 | 61 | 48.8 | 42.7 | 36.6 | 55.2 |
| DC245 (11) | | 6.1 | 12.2 | 24.4 | | 12.2 | 18.3 | 24.4 | |
| Eutanol G (15) | | | | | | | | | 13.8 |
| Perfume | 1 | 1 | 1 | 1 | 1 | 1 | 1 | 1 | 1 |
| Penetrometer Hardness (mm) | 10.4 | 12.9 | 11.1 | 11.7 | 9.8 | 9.4 | 10.1 | 10.5 | 16.5 |
| Whiteness on Black Wool | n/d | 24.4 | 21.8 | 24.9 | 22.1 | 22.1 | 21.5 | 23.3 | 21.3 |
| Whiteness on grey abrasive paper | n/d | 32.6 | 33.6 | 35.6 | 31.2 | 33.4 | 34.5 | 33.3 | 23.1 |

|  | Ex 2.10 | Ex 2.11 | Ex 2.12 | Ex 2.13 | Ex 2.14 | Ex 2.15 | Ex 2.16 | Ex 2.17 | Ex 2.18 |
|---|---|---|---|---|---|---|---|---|---|
| 12-HSA (6) | | 6 | 4 | | | | | | |
| GP-1 (7) | 2 | | 6 | 6 | | | | | |
| Montan Acid Wax (17) | 6 | 3 | | | | | | | |
| K82H (3) | | | | | 10 | 10 | 10 | 8 | 8 |
| AZAG 7167 (8) | 24 | 24 | 25 | 25 | 24 | 24 | 24 | 24 | 24 |
| Finsolv TN (10) | 53.6 | 66.0 | 65 | 60 | 47.2 | 41.3 | 35.4 | 59 | |
| Finsolv BOD (20) | | | | | | | | | 61 |

TABLE 2-continued

| | | | | | | | | | |
|---|---|---|---|---|---|---|---|---|---|
| Prisorine 3515 (16) | | | | | 9 | | | | |
| Eutanol G (15) | 13.4 | | | | | | | | |
| Perfume | 1 | 1 | | | 1 | 1 | 1 | 1 | 1 |
| Penetrometer Hardness (mm) | 11.8 | 13.5 | 10.3 | 17.6 | 8.8 | 8.8 | 10.0 | 7.7 | 7.1 |
| Whiteness on Black Wool | 20.3 | 18.8 | 16.6 | 19.1 | 15.0 | 14.8 | 14.8 | 23.1 | 15.1 |
| Whiteness on grey abrasive paper | 28.1 | 30.6 | 30.7 | 32.8 | nm | nm | nm | nm | 35.1 |

The sticks obtained in Example 2.1 to 2.18 each left virtually no white deposits when applied to skin.

EXAMPLE 3

Non-opaque Sticks

The formulations and resultant properties of sticks made in Example 3 are summarised in Table 3 below.

TABLE 3

| | Ex 3.1 | Ex 3.2 | Ex 3.3 | Ex 3.4 | Ex 3.5 | Ex 3.6 |
|---|---|---|---|---|---|---|
| 12-HSA (6) | 10 | | | | 6 | 6 |
| GP-1 (7) | | 6 | 6 | 6 | 2 | 2 |
| AZAG 7167 (8) | | | | | 24 | 24 |
| AACH A418 (18) | 20 | 20 | 20 | 20 | | |
| Finsolv TN (10) | 70 | 74 | 64 | 67 | 20.4 | |
| Prisorine 3515 (16) | | | 10 | 7 | | |
| Eutanol G (15) | | | | | | 13.6 |
| DC704 (14) | | | | | 47.6 | 54.4 |
| RI AP Active | 1.534 | 1.534 | 1.534 | 1.534 | 1.562 | 1.562 |
| RI Solvent | 1.4841 | 1.4841 | 1.4803 | 1.4814 | 1.5343 | 1.5312 |
| Penetrometer Hardness (mm) | 11.9 | 12.9 | Nm | 12.5 | 3.6 | 10.4 |
| Whiteness on Black Wool | nm | 16.3 | Nm | 16.2 | 16.0 | 18.0 |
| Whiteness on grey abrasive paper | nm | 32.7 | Nm | 35.8 | 26.5 | 26.6 |

All of the sticks made in Example 3.1 to 3.6 were all slightly translucent in appearance and left virtually no white deposits when applied to skin.

EXAMPLE 4

Further wax-structured sticks were made in accordance with the general procedure of Example 1 and as summarised in Table 4 below (n/d=test not carried out).

TABLE 4

| | Ex 4.1 | Ex 4.2 | Ex 4.3 | Ex 4.4 | Ex 4.5 | Ex 4.6 | Ex 4.7 |
|---|---|---|---|---|---|---|---|
| K82H (3) | 10.4 | 10.4 | 10.4 | 10.4 | 16 | 6 | 6 |
| K62 (4) | 5.6 | 5.6 | 5.6 | 5.6 | | 6 | 6 |
| Stearyl alcohol (5) | 2 | 2 | 2 | 2 | 2 | | |
| Silicone wax (35) | | | | | | 2 | 2 |
| AZAG 908 (27) | 24 | 24 | 24 | 24 | 24 | 24 | 24 |
| Finsolv TN (10) | 57 | 24 | 26 | 56.5 | 56.5 | 61 | 59 |
| Glyceryl Stearate (32) | | 5.6 | 5.6 | | | | |
| PEG-8 Distearate (33) | | 2 | | | | | |
| DC245 (11) | | 24 | 24 | | | | |
| Silica (34) | | | | 0.5 | 0.5 | | |
| Perfume | 1 | 1 | 1 | 1 | 1 | 1 | 1 |
| Properties | | | | | | | |
| Penetrometer Hardness (mm) | 4.5 | n/d | n/d | 5.8 | 5.2 | 6.2 | 8.6 |
| Whiteness on Black Wool (24 hrs) | 18.0 | 20.1 | 19.5 | 18.4 | 16.2 | 15.2 | 15.1 |
| Whiteness on grey Wet or Dry paper (24 hrs) | 32.4 | 31.3 | 31.3 | 33.1 | 34.0 | 32.5 | 32.2 |

Measurement of Properties i) Hardness of a Stick Using a Penetrometer

The hardness and rigidity of a composition which is a firm solid can be determined by penetrometry.

A suitable procedure is to utilises a lab plant PNT penetrometer equipped with a Seta wax needle (weight 2.5 grams) which has a cone angle at the point of the needle specified to be 9°10'±15'. A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test of this nature, an appropriate hardness for use in an open-ended dispensing container is a penetration of less than 30 mm in this test, for example in a range from 2 mm to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Deposition and Whiteness of Deposit

Deposition

Another test of the properties of a composition is the amount of the composition which is delivered onto a surface when the composition is drawn across that surface (representing the application of a stick product to human skin). To carry out this test of deposition, a sample of the composition with standardised shape and size is fitted to apparatus which draws the sample across a test surface under standardised conditions. The amount transferred to the surface is determined as an increase in the weight of the substrate to which it is applied. If desired the colour, opacity or clarity of the deposit may subsequently be determined.

A specific procedure for such tests used apparatus to apply a deposit from a stick onto a substrate under standardised conditions and then measures the mean level of white deposits using image analysis.

The substrates used were a: 12×28 cm strip of black Worsted wool fabric.

b: 12×28 cm strip of grey abrasive paper (3M™ P800 WetorDry™ Carborundum paper)

The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to biased the stick against the substrate with a standardised force. The apparatus was operated to pass the stick laterally across the substrate eight times. The substrate was carefully removed from the rig and re-weighed.

Whiteness of Deposit

The deposits from the previous test were assessed for their whiteness after an interval of 24 hours approximately.

This was done using a Sony XC77 monochrome video camera with a Cosmicar 16 mm focal length lens positioned vertically above a black table illuminated from a high angle using fluorescent tubes to remove shadowing. The apparatus was initially calibrated using a reference grey card, after the fluorescent tubes had been turned on for long enough to give a steady light output. A cloth or Carborundum paper with a deposit thereon from the previous test was placed on the table and the camera was used to capture an image. An area of the image of the deposit was selected and analysed using a Kontron IBAS image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen.

Refractive Index

The refractive index of a liquid was measured using a standard refractometer at 22° C.

The refractive index of a particulate solid was measured at 22° C. using a comparative method in which the particulate material was suspended in a range of fluids of known refractive index, and the mixture which gave the highest clarity to the eye of a skilled person was taken to be the refractive index of the particulate solid.

EXAMPLE 4

Further wax-structured sticks were made in accordance with the general procedure of Example 1 and as summarised in Table 4 below.

|  | Ex 4.1 | Ex 4.2 | Ex 4.3 | Ex 4.4 | Ex 4.5 | Ex 4.6 | Ex 4.7 |
| --- | --- | --- | --- | --- | --- | --- | --- |
| K82H (3) | 10.4 | 10.4 | 10.4 | 10.4 | 16 | 6 | 6 |
| K62 (4) | 5.6 | 5.6 | 5.6 | 5.6 |  | 6 | 6 |
| Stearyl alcohol (5) | 2 | 2 | 2 | 2 | 2 |  | 2 |
| Silicone wax (35) |  |  |  |  |  | 2 | 2 |
| AZAG 908 (27) | 24 | 24 | 24 | 24 | 24 | 24 | 24 |
| Finsolv TN (10) | 57 | 24 | 26 | 56.5 | 56.5 | 61 | 59 |
| Glyceryl Stearate (32) |  | 5.6 | 5.6 |  |  |  |  |
| PEG-8 Distearate (33) |  | 2 |  |  |  |  |  |
| DC245 (11) |  | 24 | 24 |  |  |  |  |
| Silica (34) |  |  |  | 0.5 | 0.5 |  |  |
| Perfume | 1 | 1 | 1 | 1 | 1 | 1 | 1 |
| Properties | | | | | | | |
| Penetrometer Hardness (mm) | 4.5 | n/d | n/d | 5.8 | 5.2 | 6.2 | 8.6 |
| Whiteness on Black Wool (24 hrs) | 18.0 | 20.1 | 19.5 | 18.4 | 16.2 | 15.2 | 15.1 |
| Whiteness on grey Wet or Dry paper (24 hrs) | 32.4 | 31.3 | 31.3 | 33.1 | 34.0 | 32.5 | 32.2 |

We claim:

1. An anhydrous antiperspirant formulation comprising a particulate antiperspirant suspended in a water-immiscible carrier fluid which is structured by an effective amount of a structurant, in which at least 45% by weight of said carrier fluid comprises an oxygen-containing emollient oil of higher RI having a refractive index of at least 1.465, and said structurant comprises a wax or a non-polymeric fibre-forming gellant other than 12-hydroxystearic acid alone or in combination with stearic acid or a polymeric alkylmethylsiloxane obeying formula (I) or (II) or a combination of β-sitosterol and γ-oryzanol.

2. An antiperspirant stick according to claim 1 in which the carrier fluid comprises at least 60% by weight of said emollient oil of higher RI.

3. An antiperspirant stick according to claim 1 in which the carrier fluid is deficient in or free from an alkoxy cinnamate.

4. An antiperspirant stick according to claim 1 in which the emollient oil of higher RI comprises an alkyl benzoate, an alkylene dibenzoate, an alkoxylated alkyl benzoate or a polyalkylene oxide dibenzoate, or a mixture of two or more thereof.

5. An antiperspirant stick according to claim 4, in which emollient oil of higher RI comprises an alkyl benzoate in which the alkyl group contains from 12 to 20 carbon atoms, or mixture of two or more of said alkyl benzoate compounds.

6. An antiperspirant stick according to claim 5 in which the alkyl group in the alkyl benzoate is selected from octyldodecyl, isostearyl, dodecyl to pentadecyl, and mixtures of dodecyl to pentadecyl.

7. An antiperspirant stick according to claim 4 in which the alkylene dibenzoate comprises dipropylene glycol dibenzoate.

8. An antiperspirant stick according to claim 4 in which the alkoxylated benzoate comprises polypropylene glycol stearyl ether benzoate.

9. An antiperspirant stick according to claim 8 further comprising from 10 to 20 polypropylene glycol units.

10. An antiperspirant stick according to claim 4 in which the polyalkylene oxide dibenzoate comprises a dibenzyl ester of an ethylene oxide/propylene oxide copolymer.

11. An antiperspirant stick according to claim 1 in which the emollient oil of high RI comprises a non-volatile silicone oil.

12. An antiperspirant stick according to claim 11 in which the non-volatile silicone oil comprises a polymethylphenylsiloxane.

13. An antiperspirant stick according to claim 12 further comprising an oil having a methyl: phenyl mole ratio of 1:1.

14. An antiperspirant stick according to claim 12 in which the non-volatile silicone oil comprises tetramethyltetraphenyltrisiloxane.

15. An antiperspirant stick according to claim 11 in which the non-volatile silicone oil has a viscosity of below 300 centistokes.

16. An antiperspirant stick according to claim 15 in which the non-volatile silicone oil has a viscosity of below 200 centistokes.

17. An antiperspirant stick according to claim 11 in which the non-volatile silicone oil has a Refractive Index of at least 1.50.

18. An antiperspirant stick according to claim 1 in which the emollient oil of high RI comprises from 70 to 99% by weight of the carrier fluid.

19. An antiperspirant stick according to claim 1 in which the stick contains said wax as structurant in an amount of from 10 to 25% by weight of the stick.

20. An antiperspirant stick according to claim 1 in which the stick contains as structurant one or more waxes selected from fatty alcohols, glyceride waxes, glycol ester waxes, and alkylalkanoate waxes.

21. An antiperspirant stick according to claim 20 in which the structurant comprises a combination of a glyceride wax with at least one second wax selected from glycol ester waxes, alkylalcanoate waxes and fatty alcohols.

22. An antiperspirant stick according to claim 21 in which the glyceride wax is present in a weight ratio to the second wax or waxes of 1:2 to 1:6.

23. An antiperspirant stick according to claim 22 in which the glyceride wax is present in a weight ratio to the second wax or waxes of 2:5 to 1:4.

24. An antiperspirant stick according to claim 1 in which it contains said non-polymeric fibre-forming gellant as structurant in an amount of from 4 to 12% by weight of the stick.

25. An antiperspirant stick according to claim 24 in which the non-polymeric fibre-forming gellant comprises a mixture of non-polymeric fibre-forming gellants.

26. An antiperspirant stick according to claim 25 in which the mixture of said gellants comprises 12-hydroxystearic acid and an N-alkyl-L glutamic acid di-alkylamide.

27. An antiperspirant stick according to claim 26 in which the mixture of said gellants comprises 12-hydroxystearic acid and an N-alkyl-L glutamic acid di-alkylamide having a weight ratio of the former to the latter of from 1:1 to 5:1.

28. An antiperspirant stick according to claim 1 in which the structurant comprises a mixture of wax and non-polymeric fibre-forming gellant.

29. An antiperspirant stick according to claim 28 in which the weight of wax in the stick is selected in the range of from 5 to 12%.

30. An antiperspirant stick according to claim 29 in which the wax is present in a weight ratio to the non-polymeric fibre-forming gellant of from 1:1 to 3:1.

31. An antiperspirant stick according to claim 29 in which the wax is an alkyl alkanoate wax and the non-polymeric fibre-forming gellant is 12-hydroxystearic acid.

32. An antiperspirant stick according to claim 1 which contains up to 5% by weight glycerol.

33. A process for making an antiperspirant stick comprising the steps of:

i. incorporating into a liquid carrier a structurant at an effective concentration and in an amount sufficient to structure the carrier to render it solid at 20° C.

ii. rendering the structurant-containing mixture or one or more of its constituents mobile at an elevated temperature iii. mixing the liquid carrier with an antiperspirant active to form an antiperspirant-containing mixture, steps 2 and 3 being conducted either before, after or simultaneously with step 1 iv. introducing the mobile mixture into moulding means and v. cooling or permitting the mobile mixture to cool to a temperature at which it is structured, in which at least 45% by weight of said carrier fluid comprises an oxygen-containing emollient oil having a refractive index of at least 1.465, and said structurant is a wax or a fibre-forming gellant other than 12-hydroxystearic acid alone or in combination with stearic acid or a polymeric alkylmethylsiloxane obeying formula (I) or (II) or a combination of β-sitosterol and γ-oryzanol.

34. A method of reducing or controlling axillary sweating comprising applying topically to skin an anhydrous antiperspirant formulation comprising a particulate antiperspirant suspended in a water-immiscible carrier fluid which is structured by an effective amount of a structurant, in which at least 45% by weight of said carrier fluid comprises of an oxygen-containing emollient oil of higher RI having a refractive index of at least 1.465, and said structurant is a wax or a non-polymeric fibre-forming gellant other than 12-hydroxystearic acid alone or in combination with stearic acid or a polymeric alkylmethylsiloxane obeying formula (I) or (II) or a combination of β-sitosterol and γ-oryzanol.

35. An antiperspirant product comprising an antiperspirant formulation in the form of a stick disposed within a packaging which enables a portion of the stick to be exposed for topical application to skin in which the formulation comprises a particulate antiperspirant suspended in a water-immiscible carrier fluid which is structured by an effective amount of a structurant, in which at least 45% by weight of said carrier fluid comprises of an oxygen-containing emollient oil of higher RI having a refractive index of at least 1.465, and said structurant is a wax or a non-polymeric fibre-forming gellant other than 12-hydroxystearic acid alone or in combination with stearic acid or a polymeric alkylmethylsiloxane obeying formula (I) or (II) or a combination of β-sitosterol and γ-oryzanol.

* * * * *